United States Patent [19]

Mason

[11] 4,199,081
[45] Apr. 22, 1980

[54] APPARATUS FOR DISPENSING MERCURY AND DENTAL ALLOY

[76] Inventor: Joseph E. Mason, 10 Tuxedo Dr., Melville, N.Y. 11746

[21] Appl. No.: 889,017

[22] Filed: Mar. 22, 1978

[51] Int. Cl.² ........................................... G01F 11/10
[52] U.S. Cl. ................................. 222/43; 222/137; 222/181; 222/235; 222/308; 222/309; 222/340
[58] Field of Search ............... 222/43, 137, 153, 181, 222/184, 185, 235, 276, 305, 307, 308, 309, 332, 340, 361; 366/282, 283

[56] References Cited

U.S. PATENT DOCUMENTS

| | | | |
|---|---|---|---|
| 780,680 | 1/1905 | Peterson et al. | 222/361 X |
| 1,286,881 | 12/1918 | Gray. | |
| 1,516,942 | 11/1924 | Wise. | |
| 1,605,832 | 11/1926 | Garhart. | |
| 1,714,704 | 5/1929 | Wells et al. | 222/181 X |
| 2,096,259 | 10/1937 | Orihel | 222/181 |
| 3,040,934 | 6/1962 | Weiner | 222/308 X |
| 3,168,213 | 2/1965 | DeGon | 222/137 X |
| 3,623,639 | 11/1971 | McShirley | 222/361 X |
| 3,923,085 | 12/1975 | Nimer | 222/235 X |

FOREIGN PATENT DOCUMENTS 757485  9/1965 United Kingdom.

*Primary Examiner*—David A. Scherbel
*Assistant Examiner*—Fred A. Silverberg
*Attorney, Agent, or Firm*—Norbert P. Holler

[57] ABSTRACT

Apparatus for dispensing metered amounts of mercury and silver alloy, for the production of dental amalgam, is disclosed. The apparatus can dispense the silver alloy in either tablet or powder form and is provided with a stirring member in the silver alloy powder supply container to agitate the powder during the metering and dispensing thereof so as to alleviate the problem of clumping. The apparatus also has a member to adjust the amount of mercury being dispensed and an element for locking the adjusting member securely against accidental shifting out of position.

17 Claims, 7 Drawing Figures

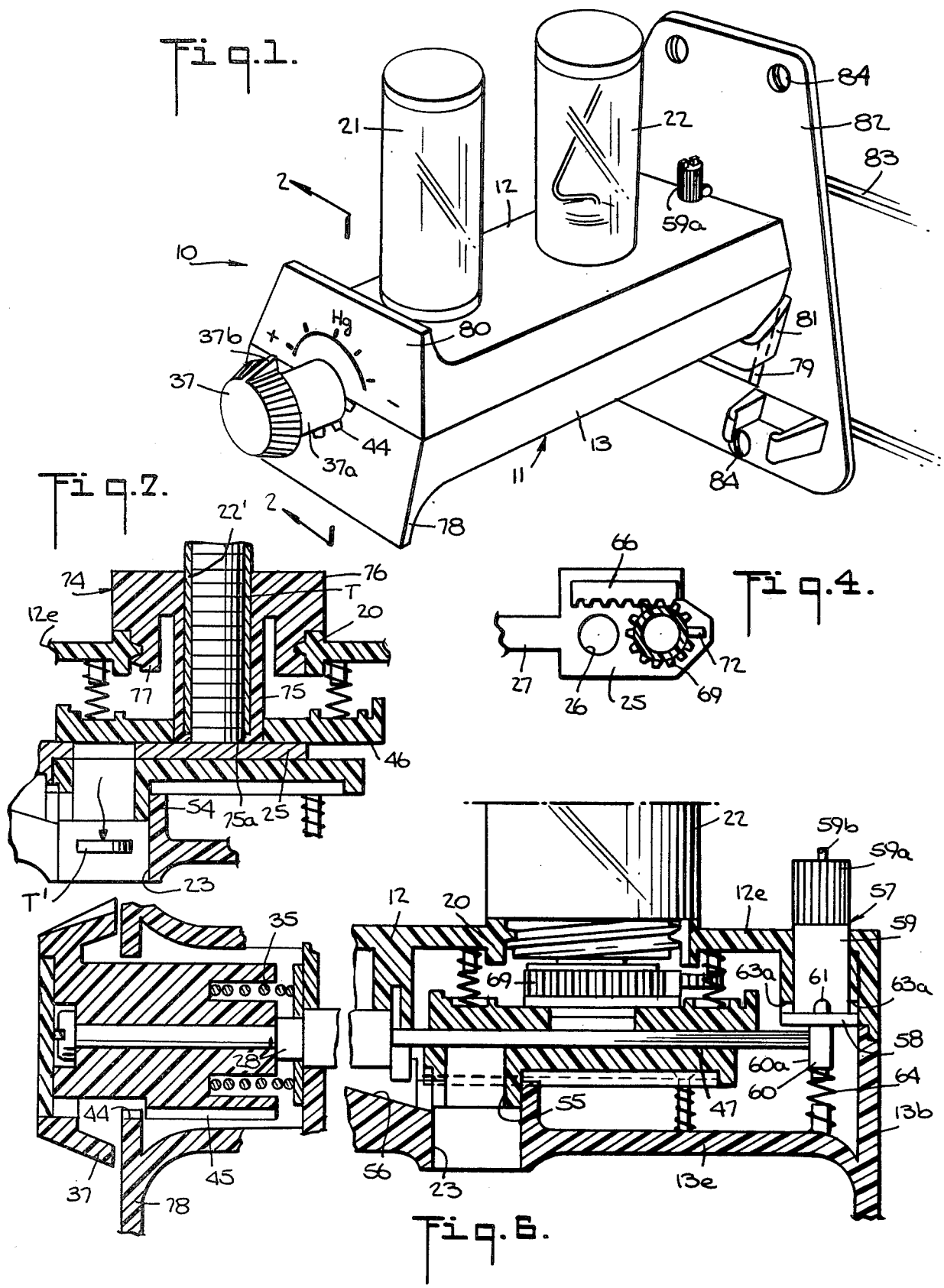

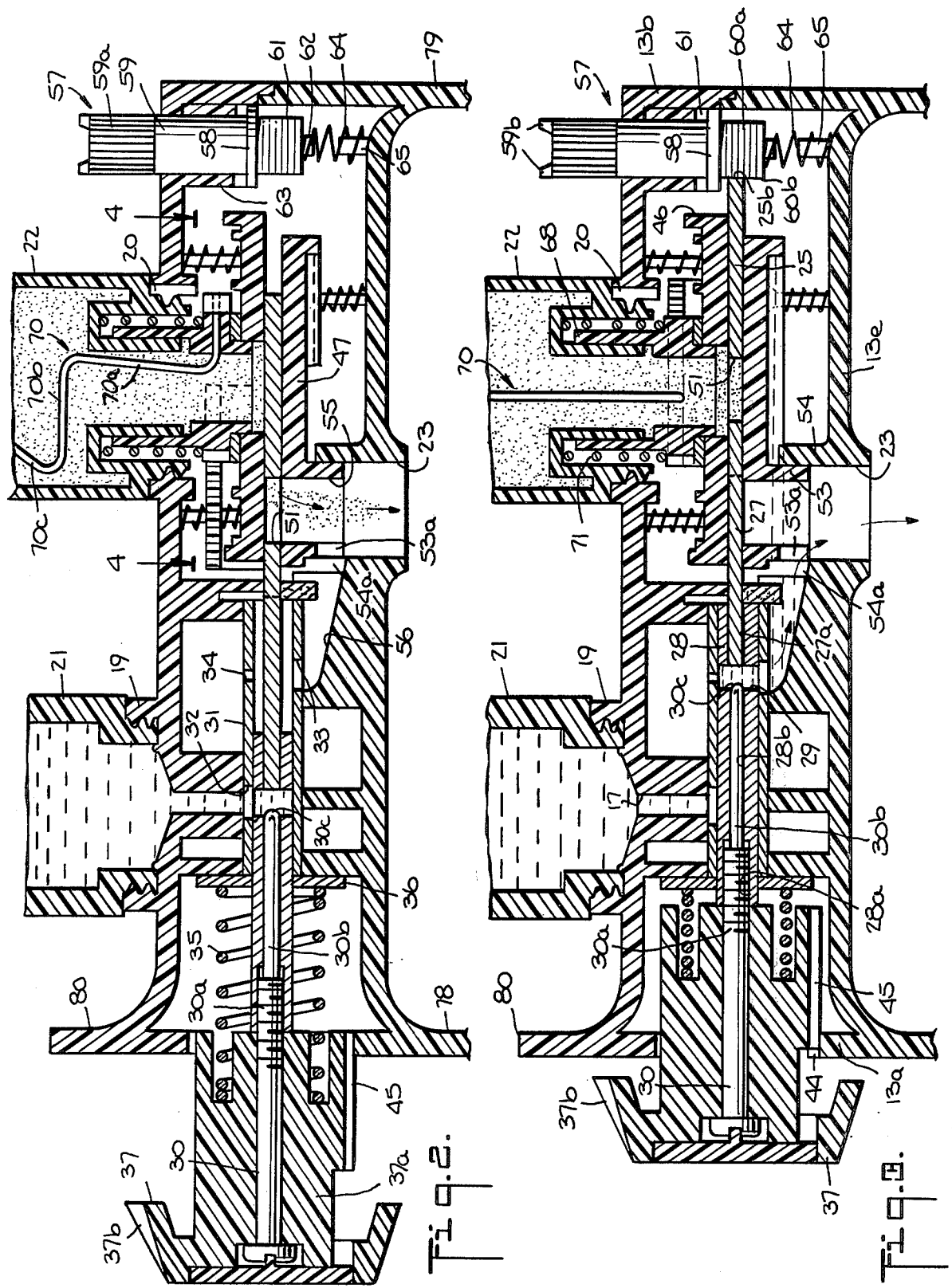

APPARATUS FOR DISPENSING MERCURY AND DENTAL ALLOY

This invention relates to apparatus for dispensing accurately metered quantities of mercury and silver alloy for use in producing a dental amalgam for dental fillings.

Apparatuses of various types for dispensing metered amounts of mercury and silver alloy for use in producing dental amalgams have been known for many years, but they are basically limited in scope, being equipped to dispense the alloy either in powder form only or in tablet form only. This creates the inconvenience and expense, however, of requiring the operator to change to a different dispenser should he decide (or be constrained by extraneous circumstances) to switch from powder to tablets or vice versa. Many of the prior art dispensers have also included means for enabling the amount of mercury being dispensed to be adjusted or varied, but the very means that provided that variation frequently tend to shift during the dispensing operation, yielding an undesired amount of dispensed mercury.

Yet another problem which has beset the prior art silver alloy powder dispensers has been that the uniformity of the amount of alloy dispensed was often disturbed by the tendency of the powder to absorb moisture and thereby to clump, preventing the gravitational flow of powder into the metering chamber. Various methods have, therefore, been attempted in order to overcome the problem of clumping. In one variation, for example, the entire dispensing apparatus must be turned over in order to enable the powder blockage to be eliminated, after which, of course, the apparatus must first be righted again before the powder can be gravitationally dispensed. In another variation, it is necessary to tap the powder supply vial a few times prior to each powder metering and dispensing operation.

It is an important object of the present invention, therefore, to provide a novel and improved apparatus for metering and dispensing mercury and silver alloy, which apparatus is adaptable for use in dispensing either silver alloy powder or silver alloy tablets.

Another object of the invention is the provision of a dispenser which is secure against inadvertent and undesired shifts in the amounts of mercury being dispensed and in which, when silver alloy powder is being dispensed, the problem of clumping is effectively overcome.

Generally speaking, the objectives of the present invention are attained by an apparatus for metering and dispensing metered amounts of mercury and silver alloy for use in producing dental amalgams, which has both means to enhance the uniformity of the amounts of mercury and silver alloy dispensed and means to adapt the apparatus to meter and dispense silver alloy in either powder or tablet form, as well as means for selectively locking in the mercury metering setting and means associated with the alloy powder dispensing capability for automatically agitating the powder during each dispensing operation.

In its basic form, the apparatus includes a housing having assembled upper and lower sections provided with respective means to define an interior guideway in which a two-chambered slide is movably mounted. The upper section of the housing has respective inlet ports, for the mercury and the silver alloy, arranged so that a vial containing mercury and either a silver alloy powder-containing or a silver alloy tablet-containing vial with an associated removable adapter can be securely mounted in position on the housing, with the apparatus thus being adapted for dispensing either silver alloy powder or silver alloy tablets. The lower section of the housing has respective mercury and silver alloy receiving passageways the inlet ends of which can communicate with the slide chambers and the discharge ends of which communicate with a common dispensing opening.

The slide includes a flat, relatively wide plate section and a hollow, relatively narrow tubular section, with the latter being open at one end and closed at the other and being connected at the closed end to one end edge of the plate section. The plate section is located beneath the silver alloy inlet port and has a relatively wide through opening formed therein to constitute the chamber for receiving the alloy being dispensed, and the tubular section extends to the exterior of the housing at one end of the latter, the portion of this section located beneath the mercury inlet port having a relatively narrow through opening formed therein to constitute the chamber for receiving the mercury being dispensed. An elongated rod having manipulating means (e.g. a slotted head) at one end and external threads over its middle region is screwed into the open end of the tubular section of the slide to such an extent that the tip of the rod is located at the junction between the interior of the tubular section and the mercury receiving chamber and can be projected to a greater or lesser extent into the latter for adjusting the volume of the chamber and thus the volume of mercury which can be received therein. Exteriorly of the housing, the rod is fixedly secured, as by bonding, to a knob to facilitate both the rotation of the rod relative to the slide and the pushing of the slide inwardly through the guideway against the outward biasing force of a suitable spring member. A plurality of keyways in the end wall of the housing through which the knob extends co-act with a key on the knob to provide means for retaining knob, and hence the mercury volume adjusting rod, non-rotatably in the various adjusted positions thereof, and an exteriorly accessible locking means is provided in the housing to prevent any shifting of the key out of any given keyway, and hence any adjustment of the mercury volume setting, unless the locking means is first deactivated.

The plate section of the slide is also provided with a longitudinally extending rack. The latter is arranged so that when the apparatus is used with a silver alloy powder-containing vial seated in the respective inlet port of the housing, the rack meshes with a pinion rotatably carried by the vial at its discharge end. The pinion is fixedly connected with a stirring member extending upwardly into the vial. This arrangement thus ensures that when the slide is longitudinally reciprocated through the guideway, the rack also moves and turns the pinion, thereby revolving the stirring member and agitating the silver alloy powder in the supply vial. When silver alloy tablets are to be dispensed, of course, stirring is not needed. The tablet-containing vial is, therefore, secured to the housing with the aid of a pinion-less adapter, so that the rack remains nonfunctional even though it still moves with the slide as before.

The foregoing and other objects, characteristics and advantages of the present invention will be more clearly understood from the following detailed description thereof when read in conjunction with the accompanying drawings, in which:

FIG. 1 is a perspective illustration of an apparatus for dispensing mercury and silver alloy according to the present invention, the apparatus being shown as equipped with a silver alloy powder-containing supply vial;

FIG. 2 is a fragmentary sectional view taken along the line 2—2 in FIG. 1 and shows the slide of the apparatus in its rest position;

FIG. 3 is a sectional view similar to FIG. 2 but shows the apparatus with the locking means active and the slide fully pushed in for a dispensing operation;

FIG. 4 is a fragmentary sectional view taken along the line 4—4 in FIG. 2;

FIG. 6 is a sectional view similar to FIG. 3 but shows the apparatus with the locking means deactivated and the slide pushed in somewhat further for a mercury volume adjusting operation; and FIG. 7 is a fragmentary sectional view of the alloy-dispensing portion of the apparatus but shows a tablet-containing vial and its mounting adapter substituted for the powder-containing vial.

Figure 5:
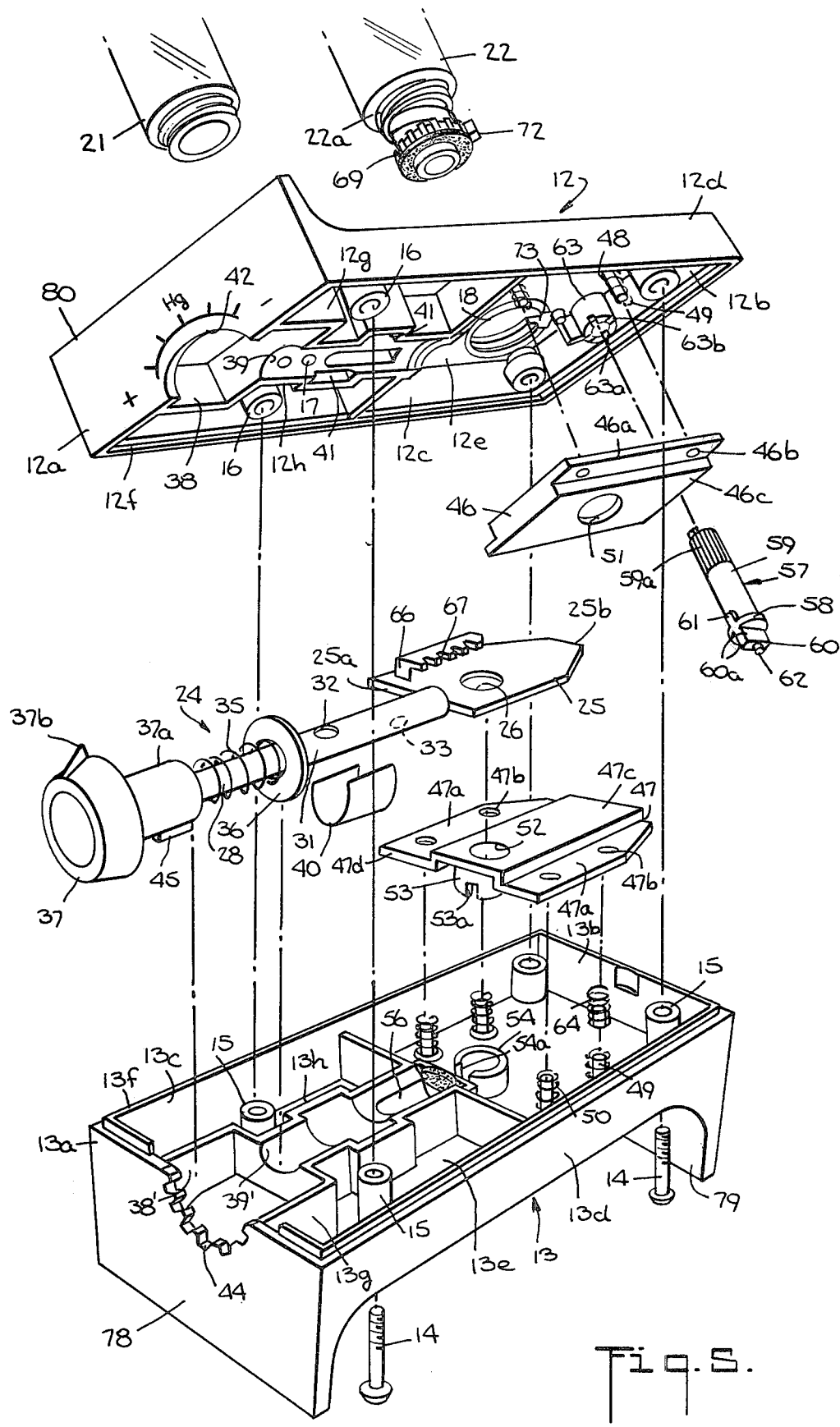
FIG. 5 is an exploded perspective view of the apparatus shown in FIG. 1.

Referring now to the drawings in greater detail, a mercury and silver alloy dispenser 10 according to the basic aspects of the present invention comprises (FIGS. 1 and 5) a housing 11 of generally rectangular configuration and composed of rigid upper and lower sections 12 and 13 advantageously injection molded of any chemically inert and non-toxic synthetic plastic material such as ABS resin. The upper housing section 12 has front and rear walls 12a and 12b, sidewalls 12c and 12d, and a top wall 12e, and is downwardly open. Correspondingly, the lower housing section 13 has front and rear walls 13a and 13b, sidewalls 13c and 13d, and a bottom wall 13e, and is upwardly open. To ensure that the housing sections when assembled will be properly positioned relative to one another, a peripheral recess 12f is provided along the bottom edge of the upper housing section 12, and a corresponding peripheral ridge 13f is provided along the top edge of the lower housing section 13. In the assembled condition of the housing 11, the sections 12 and 13 are secured to one another by means of a plurality of screws 14 extending upwardly through respective openings in the bottom wall 13e and corresponding aligned tubular bushings 15 arranged on the bottom wall 13e, and thence into respective internally threaded bushings or nuts 16 fixedly mounted on the top wall 12e.

The upper housing section 12 is further provided in the top wall 12e thereof (see also FIGS. 2 and 3) with a relatively small mercury inlet port 17 and a relatively larger silver alloy inlet port 18, these being surrounded at the exterior of the top wall by respective annular mounting structures 19 and 20 (internally screw-threaded ones are shown but other expedients may obviously be used) which are adapted to receive the correspondingly configured lower discharge ends of a mercury-containing supply vial 21 and a silver alloy-containing supply vial 22. Correspondingly, the lower housing section 13 is provided in its bottom wall 13e with an outlet or discharge port 23 through which the mercury and silver alloy being dispensed can be permitted to flow gravitationally into the dentist's mixing receptacle (not shown).

In order to control the flow of mercury and silver alloy from their respective supply vials 21 and 22 to the discharge port 23, a two-chambered slide or control valve 24 is arranged interiorly of the housing 11. As best shown in FIGS. 2, 3 and 5, the slide 24, which is preferably made of stainless steel or the like, includes a relatively wide, plate-shaped first gate or valve member 25 which is provided intermediate its front and rear end edges 25a and 25b (but closer to the former and somewhat offset toward one side edge) with a through opening 26. A narrow flat-faced extension 27 of the valve member 25 at the front end edge 25a of the latter has its remote end region 27a fixedly secured to one end of a second gate or valve member 28. In the illustrated embodiment of the invention, the member 28 is tubular in form and has an axial bore extending therethrough, the bore having a relatively short, internally threaded, front end section 28a and a relatively longer smooth-walled section 28b of slightly reduced diameter extending to the rear end of the member 28. In practice, therefore, the member 25 is affixed to the member 28 by the front end region 27a of the extension 27 being fitted into the rear end region of the bore section 28b and being secured therein in any suitable fashion, as by a friction fit or by welding. The member 28 is further provided with a transverse through opening 29 just forwardly of the front end of the extension 27.

The slide or control valve 24 further includes a screw-headed pin 30 which is externally threaded over an intermediate section 30a thereof and has a somewhat reduced diameter end section 30b. Of these, the pin section 30a is screwed into the bore section 28a of the member 28, while the pin section 30b extends smoothly slidably through and completely fills the bore section 28b and terminates in a tip 30c projecting slightly into the transverse through hole 29. Freely slidably mounted on the tubular valve member 28 is a bearing sleeve 31 which is provided intermediate its ends with three radial openings, a relatively large inlet opening 32 near the front end of the sleeve, a relatively large discharge opening 33 near the rear end of the sleeve but on the side thereof diametrally opposed to the opening 32, and a relatively small vent opening 34 opposite the discharge opening 33. The sleeve is normally maintained in abutment at its rear end with the front edge 25a of the valve member 25 by means of a compression spring 35 surrounding the valve member 28 and interposed between a washer 36 bearing against the front end of the sleeve and a rear abutment surface of the hub 37a of a knob or push button 37 fixed, as by bonding, to the headed end section of the pin 30, the arrangement being such that in this disposition of the sleeve the inlet opening thereof is in alignment with the through opening 29 in the valve member 28.

As best shown in FIG. 5, for the purpose of operatively disposing the slide 24 in the housing 11, the upper and lower sections 12 and 13 are provided with respective pairs of generally longitudinally extending stepped interior walls 12g–12h and 13g–13h defining, respectively, opposed substantially square or rectangular front end chambers 38 and 38' and opposed generally semicircular longitudinal troughs or channels 39 and 39'. In the illustrated embodiment of the invention, the entire slide is secured to the upper housing section 12 by means of a generally U-shaped steel spring clip 40 (omitted from FIGS. 2 and 3 for the sake of simplicity), the bend of the clip passing under the sleeve 31 intermediate the locations of the openings 32 and 33, and the ends of the clip being suitably received in a pair of anchoring recesses 41 provided in the walls 12g and 12h adjacent the opposite sides of the channel 39. When the slide is so mounted, the opening 32 in the sleeve 31 is disposed directly below the mercury inlet port 17. To accommodate the hub of the knob or push button 37, the end wall 12a of the upper housing section 12 is provided with a semi-circulator recess 42, and correspondingly the front and wall 13a of the lower housing section 13 is provided with a semi-circular recess 43, the latter, however, being provided with a plurality of axial grooves or keyways 44. The keyways 44 are designed to accommodate an axial key 45 of predetermined length provided on the rear end region of the hub 37a of the knob or push button 37.

The arrangement thus is such that when the key 45 is not confined within any of the keyways 44 (the means for enabling this condition to be attained will be described presently), the knob or push button 37 and therewith the pin 30 can be rotated in one sense or the other so that, by virtue of the resultant screw movement of the pin section 30a in the bore section 28a of the tubular valve member 28, the pin tip 30c will be either protracted further into or retracted further out of the opening 29. On the other hand, when the key is confined in one of the keyways, the knob is effectively constrained or locked against rotation and is maintained in the respective selected position of angular adjustment, which concomitantly prevents any linear adjustment of the pin 30 and thus any variation of the volume of the mercury-receiving chamber constituted by the opening 29.

The plate-shaped valve member 25 of the slide or control valve 24 is slidably confined between a pair of anti-friction bearing plates 46 and 47 made, for example, of nylon or polytetrafluoroethylene or the like. These plates are mounted in the upper and lower housing sections 12 and 13, respectively, and are yieldingly biased toward one another. Thus, the plate 46 along one side edge thereof has a longitudinal flange 46a in which are provided two holes 46b through which extend a pair of laterally flanged or headed vertical posts 48 secured to the top wall 12e, and a pair of small compression springs 48' surround the posts 48 between the top wall and the flange 46a and press the latter downwardly, with the heads on the posts 48 ensuring retention of the plate 46 thereon. Correspondingly, the plate 47 along its opposite side edges has a pair of flanges 47a in which are provided four holes 47b through which extend four similar laterally flanged or headed posts 49 secured to the bottom wall 13e, and respective small compression springs 50 surround the posts 49 between the bottom wall and the flanges 47a and press the latter upwardly, with the heads on the posts 49 ensuring retention of the plate 47 thereon. The relatively higher central portions 46c and 47c of the plates 46 and 47 thus are maintained in continuous frictionless sliding contact with the valve member 25.

In essence, therefore, the bearing sleeve 31 and the bearing plates 46 and 47, in conjunction with their respective supporting channels 39–39' and mounting posts 48–49, define a guideway for the slide 24 through which the latter can be reciprocally displaced.

Referring further to FIGS. 2 and 5, the bearing plate 46 is provided in the central portion 46c thereof with a medial opening 51 which underlies the silver alloy inlet port 18. The bearing plate 47 likewise is provided in the central portion 47c thereof with an opening 52, but the latter is located adjacent the front end edge 47d of the plate, i.e. not in vertical registry with the opening 51. The arrangement here is such that when the slide is in its normal or rest position, as shown in FIG. 2, the silver alloy-receiving chamber constituted by the opening 26 is disposed over the opening 52 and thus forwardly of and out of communication with the silver alloy inlet port 18. The plate 47 is further provided with a cylindrical funnel or extension 53 immediately below the opening 52. The funnel 53 is dimensioned to fit into a cylindrical bushing 54 extending upwardly from the bottom wall 13e of the lower housing section 13 immediately above the discharge port 23, the funnel thus defining one passageway 55 leading to and communicating with the discharge port 23.

The funnel 53 is also provided, at a frontwardly facing portion thereof, with a recess 53a, and the bushing 54 in the corresponding frontwardly facing portion thereof is provided with a recess 54a, the arrangement being such that when the plate 47 is in position in the lower housing section 13, the recesses 53a and 54a are in precise alignment with one another and constitute the terminal opening of another, downwardly slanted passageway 56, defined between the rearwardmost end regions of the walls 13g and 13h, leading to the discharge port 23. The entrance end of the passageway 56 is in communication with the discharge opening 33 provided in the rear end region of the bearing sleeve 31.

For reasons which will become clear presently, it is contemplated by the present invention to provide for a movement of the slide 24 from its rest position to two separate displaced positions. The first of these positions is reached at the end of the operating stroke of the slide 24, i.e. its movement during and for the purpose of a dispensing operation, and is shown in FIG. 3. To define this position, the dispenser 10 according to the present invention is further provided with an adjustable abutment means 57 at the rear end of the housing 11. The abutment means 57 is a rod-shaped member having a peripheral flange or ridge 58 intermediate its ends, the upper portion 59 of the member being of circular cross-section and terminating in a knurled head or grip 59a. The lower portion 60 of the member is of substantially rectangular cross-section with a pair of opposed flat faces 60a, the thickness of the lower portion 60 being less than the diameter of the upper portion 59. The member 57 is further provided on the upper surface of the flange 58 with a pair of diametrically opposed projections 61, and on the bottom edge of the lower portion 60 with an axial projection 62.

The upper portion of the member 57 extends freely rotatably upwardly out of the upper housing section 12 via a cylindrical bushing 63 in the bottom edge of which are provided one pair of small diametrically opposed notches 63a aligned longitudinally of the housing 11 and a second pair of diametrically opposed notches 63b aligned transversely of the housing. The projection 62 is received in the upper end of a small compression spring 64 the lower end of which is seated on a small mounting post 65 extending upwardly from the bottom wall 13e of the lower housing section 13. The spring biases the member 57 upwardly so as to tend to maintain the flange 58 against the bottom edge of the bushing with the projections 61 on the flange received and seated in either the notches 63a or the notches 63b.

It will be understood, therefore, that when the member 57 is arranged as shown in FIGS. 2 and 3, with the flat faces of the lower portion 60 oriented longitudinally of the housing and with the projections 61 received in the pair of notches 63a of the bushing 63, the slide can move inwardly only until it reaches the position (its first displaced position) where one of the lateral edges 60b of the portion 60 is engaged by the rear end edge 25b (FIG. 3) of the plate-shaped valve member 25. During this movement, of course, the mercury-receiving chamber 29 is shifted from its starting position under the inlet opening 32 of the bearing sleeve 31 to a position between the discharge and vent openings 33 and 34 of the sleeve, while the silver alloy-receiving chamber 26 is shifted from its starting position above the opening 52 in the lower bearing plate 47 to a position under the opening 51 in the upper bearing plate 46.

Referring further to FIG. 3, it will also be noted that the length of the key 45 on the hub 37a of the knob or push button 37 is sufficient to ensure that even at the end of the operating stroke of the slide, the key is still confined in a respective one of the keyways 44 (FIG. 3). Accordingly, as long as the member 57 remains in its orientation shown in FIGS. 2 and 3 and blocks movement of the slide past its first displaced position, rotation of the knob or push button 37, and thus also any shifting of the mercury volume-adjusting pin 30, is effectively impossible and the volume of the mercury-receiving chamber 29 remains constant. Occasionally it may be desired, however, to change the amount of mercury to be admitted into the chamber 29 and dispensed. To enable this change to be effected, the member 57 is depressed against the force of the spring 64 until the projection 61 have been displaced completely out of their respective notches 63a. The member 57 is then rotated a quarter of a turn in the bushing 63 and thereupon released, as a result of which it will be pressed upwardly again by the spring 64 until the flange 58 engages the bottom edge of the bushing 63 but with the projections 61 now received in the transversely aligned pair of notches 63b and the flat surfaces 60a of the lower portion 60 of the member oriented transversely of the housing and the direction of movement of the slide 24.

As shown in FIG. 6, therefore, with the member 57 in the new orientation thereof, when the knob or push button 37 is pushed inwardly, the slide is able to move past the first displaced position and to a second displaced position in which the edge 25b of the valve member 25 engages the frontwardly directed one of the flat surfaces 60a, the added distance corresponding essentially to the radial distance between the peripheral edge of the flange 58 and the said frontwardly directed flat surface 60a. This, it can be seen, will be just sufficient to ensure that the key 45 is completely withdrawn from the confines of its keyway 44.

With the slide at its said second displaced position, the knob or push button 37 can be rotationally moved to bring the key 45 into alignment with any selected one of the other of the keyways 44, which condition will be indicated by the alignment of an indicator projection 37b on the knob with a selected one of the index markings of the "Hg" scale provided on the front end wall 12a of the upper housing section 12. Such angular or rotary movement of the knob will, of course, simultaneously shift the pin 30 in one sense or the other from its previous setting and will thereby either decrease or increase the volume of the mercury-receiving chamber 29 by an amount depending on the increased or decreased degree to which the pin tip region 30c projects into the chamber. Thereupon, once the desired new mercury setting has been reached, the knob is released and the spring 35 automatically returns the slide to its rest position with the key 45 now confined in its new keyway 44. Finally, the member 57 is again depressed and rotated a quarter turn in one direction or the other to bring the lower portion 60 thereof back to the orientation shown in FIGS. 2 and 3. Movement of the slide past its first displaced position is then again impossible, as is the shifting of the key 45 from its then associated keyway 44, so that the mercury volume being dispensed in each operation of the slide remains constant and secure against inadvertent variation. In this connection, in order to enable the operator to tell in which of its adjusted positions the abutment member 57 is found, the latter is provided at the end of the head 59a with a pair of aligned projections 59b oriented, for example, in the same direction as the flat faces 60a.

Referring now again to FIG. 5, suitably affixed to the plate-shaped valve member 25 adjacent to one of the side edges thereof and projecting upwardly therefrom is a rack 66 the teeth 67 of which project inwardly over the valve member 25. The rack 66 is intended for use in conjunction with the dispensing of silver alloy in powder form. To this end, the silver alloy powder supply vial 22 of the dispenser 10 according to the present invention has a reduced diameter lower end extension 22a (in the illustrated embodiment this entension is externally threaded to enable the vial 22 to be screwed into the correspondingly internally threaded silver alloy inlet port 18), into which extension is loosely fitted the tubular hub 68 of a pinion or spur gear 69. Advantageously, both rack 66/67 and the gear member 68/69 are molded of a suitable synthetic plastic material such as nylon.

Fixed to the hub 68 interiorly thereof and extending upwardly therethrough into the lower region of the vial 22 is a stiff wire member 70. The member 70 has a first portion 70a extending from the anchoring point along one side of the hub 68, a second portion 70b extending laterally from the first portion toward the opposite side of the vial, and a third portion 70c extending from the second portion at an angle upwardly and across the vial back toward the side thereof above the anchoring point of the member 70 (FIG. 2). Interposed between the hub 68 and the end extension 22a of the vial is a compression spring 71 which bears against the gear and normally biases the same downwardly relative to the vial, but the location of the juncture between the portions 70b and 70c of the member 70 over one side of the upper end of the extension 22a prevents complete withdrawal of the gear hub from the vial. The arrangement is such that when a powder-containing vial 22 has been fully and tightly positioned in the silver alloy inlet port 18, the pinion 69 and rack 67 are in mesh with each other. It will be understood, therefore, that when the slide 24 is being shifted out of and back to its rest position in the course of a dispensing operation, the movement of the rack causes the gear to be turned and therewith also the member 70. The latter thus is rotatably moved through the mass of powder in the vial 22 and agitates the same, thereby acting to disintegrate any clumps of powder which may have formed.

As best shown in FIG. 5, the gear 69 also has a laterally projecting lug 72, and a cooperating notch or recess 73 is provided at one side of the inlet port 18 to accommodate the lug during insertion and extraction of the vial from the port. It will be understood that when the vial 22 is being mounted on or removed from the housing 11, this can be done only upon alignment of the lug and notch with one another, and further that the lug will also act as a safety catch when the vial is being loosened to prevent it from accidentally falling out of the port until the lug and notch have been again brought into alignment with one another. This safety feature is of significance when a vial still at least partly filled with silver alloy powder is to be removed from the housing for one reason or another and the latter is inverted so as to prevent the powder from falling out of the vial.

As previously mentioned, the dispenser 10 according to the present invention, unlike prior art dispensers, is adapted for dispensing silver alloy not only in powder form but also in tablet form. To this end, when silver alloy tablets are to be dispensed, the powder vial 22 and its gear or pinion 69 are removed from the housing and replaced by a tablet-containing vial 22'. As shown in FIG. 7, the vial 22' has the form of an elongated glass or plastic tube in which the silver alloy tablets T are stacked. Such a vial, of course, does not require a stirring or agitating member, so that the gear 69 is unnecessary. The dispenser 10 is, therefore, provided with an adapter 74 which includes a tubular portion 75 and a knurled knob-shaped head 76. The latter has a downwardly depending skirt 77 provided with threads on its exterior surface to enable it to be screwed into the silver alloy inlet port 18. The inner diameter of the tubular portion 75 is slightly larger than the outer diameter of the tablet-containing tube 22', and ajacent its lower end the tubular portion has a small interior flange 75a defining a seat for supporting the bottom end edge of the tablet-containing vial.

The operation of the dispenser 10 according to the present invention, whether the silver alloy to be dispensed is in powder or tablet form, will be readily understood from the foregoing description. To summarize briefly, at the start, the slide 24 is in its rest position (FIG. 2) and the two vials 21 and 22 (or 22'-74) are in place and supported by their respective mounting means 19 and 20. The chamber 29 thus is filled with mercury to the extent permitted by the volume-adjusting pin tip 30c, while the chamber 26 is empty. The knob 37 is then pushed in to shift the slide to its first displaced position (FIG. 3), so that the mercury trapped in the chamber 29 flows out of the same and into the passageway 56 and thence through the discharge port 23 into the mixing receptacle (not shown), while the desired quantity of silver alloy powder (or tablet) drops into the chamber 26. Upon release of the knob 37, the slide returns to its rest position under the action of the spring 35, at which time the silver alloy (either the powder as shown in FIG. 2 or the tablet T' as shown in FIG. 7) falls into the passageway 55 and thence through the discharge port 23 into the mixing receptacle.

Referring further to FIGS. 1 and 5, it will be seen that the lower section 13 of the dispenser housing 11 has its front and rear end walls 13a and 13b extended downwardly below the plane of the bottom wall 13e, as indicated at 78 and 79. These extensions are preferably of identical height and thus constitute a pair of feet by which the dispenser can be positioned on any suitable supporting surface. If this expedient is used, of course, the dispenser will have to be hand-held during the performance of a dispensing operation, with the index and middle finger of one hand engaged behind the extension 78 and the corresponding upward extension 80 of the front wall 12a of the upper housing section 12 and the thumb pressing on the knob 37. As an alternative, however, the rear extension 79 is also adapted to be received in a bracket 81 provided at the front face of a wall mounting plate 82 affixed to a vertical wall or other support 83 by means of screws 84, so that the otherwise required manipulation of the housing before, during and after the dispensing operation is effectively avoided.

It will be understood that the foregoing description of a preferred embodiment of the present invention is for purposes of illustration only, and that the various structural and operational features herein disclosed are susceptible to a number of modifications and changes none of which entails any departure from the spirit and scope of the present invention as defined in the hereto appended claims.

What is claimed is:

1. A device for dispensing a metered amount of mercury and a metered amount of silver alloy in either powder or tablet form, comprising:

a housing having upper and lower interconnected sections;

said upper housing section being provided with a mercury inlet port, a silver alloy inlet port, first mounting means associated with said mercury inlet port for supporting a mercury supply vial on said upper housing section in discharging relation to said mercury inlet port, second mounting means associated with said silver alloy inlet port for supporting on said upper housing section in discharging relation to said silver alloy inlet port a silver alloy powder supply vial, and an adapter removably securable to said second mounting means for selectively enabling the latter to support on said upper housing section in discharging relation to said silver alloy inlet port a silver alloy tablet supply vial;

said lower housing section being provided with a discharge port and with respective means defining first and second passageways for enabling gravitational flow of mercury and silver alloy to said discharge port;

means defining a guideway in said housing, a slide mounted in said guideway for reciprocal movement within said housing between a rest position and first and second displaced positions, and a knob connected with said slide and projecting exteriorly of said housing for enabling manual displacement of said slide;

said slide including first and second valve members for controlling the flow of mercury and silver alloy, respectively, between said inlet ports and said first and second passageways, said first valve member being provided with a first transverse through opening to constitute a mercury-receiving chamber, and said second valve member being provided with a second through opening to constitute a silver alloy-receiving chamber, said slide when in said rest position thereof disposing said mercury-receiving chamber in communication with said mercury inlet port and said silver alloy-receiving chamber in communication with said second passageway, and said slide when in said first displaced position thereof disposing said mercury-receiving chamber in communication with said first passageway and said silver alloy-receiving chamber in communication with said silver alloy inlet port;

spring means arranged in said housing and biasing said slide in the direction of said rest position thereof;

means connected with said first valve member and shiftable by said knob for adjusting the volume of said mercury-receiving chamber;

adjustable abutment means mounted in said housing and operable selectively either to block movement of said slide past said first displaced position thereof or to permit movement of said slide past said first and to said second displaced position thereof; and means acting on said slide for locking said volume adjusting means against shifting whenever said abutment means is adjusted to block movement of said slide past said first displaced position thereof and for permitting shifting of said volume adjusting means whenever said abutment means is adjusted to permit movement of said slide to said second displaced position thereof.

2. A device as claimed in claim 1, further comprising a silver alloy powder supply vial supported by said second mounting means and having a lower portion extending through said silver alloy inlet port into said upper housing section, a stirring member disposed in said upper housing section and extending up into said silver alloy powder supply vial, and cooperating gear means interconnected between said slide and said stirring member for effecting an oscillatory movement of said stirring member upon reciprocal movement of said slide, thereby to agitate the silver alloy powder and counteract the tendency of the silver alloy powder to clump.

3. A device as claimed in claim 2, wherein said cooperating gear means comprises a rack and pinion combination, said rack being fixedly secured to and movable with said second valve member, and said pinion being supported by said silver alloy powder supply vial and rotatable relative thereto, said stirring member being fixedly secured to said pinion and movable therewith.

4. A device as claimed in claim 3, wherein said lower portion is of reduced diameter relative to the remainder of said silver alloy powder supply vial and defines an annular shoulder therein, said pinion comprises a tubular hub freely rotatably and axially displaceably extending into said lower portion of said silver alloy powder supply vial, spring means are interposed between said pinion and said silver alloy powder supply vial for biasing said hub of the former outwardly of the latter, and said stirring member is a stiff wire fixedly connected to the interior of said hub and has a pair of mutually inclined portions located within the confines of said silver alloy powder supply vial with the juncture between said portions overlying said shoulder for inhibiting separation of said hub and said pinion from said silver alloy powder supply vial.

5. A device as claimed in claim 1, wherein said first valve member is a rod connected at one end of said second valve member and having said mercury-receiving chamber located adjacent said one end, said rod further having a longitudinal bore extending from the other end of said rod to said mercury-receiving chamber and being internally threaded adjacent said other end, and said volume adjusting means comprises a pin located in said bore with a close sliding fit and with its tip end region located at the juncture between said bore and said mercury-receiving chamber, said pin further having an intermediate externally threaded region screwed into the threaded section of said bore and having a head end region located exteriorly of said bore beyond said other end of said rod and fixedly connected with said knob, whereby rotation of said knob and therewith of said pin in one sense or the other causes the extent to which said tip end region of said pin projects into said mercury-receiving chamber to be either increased or decreased to either decrease to increase the volume of said mercury-receiving chamber.

6. A device as claimed in claim 5, wherein said knob has a hub extending through a wall opening of said housing, and said locking means comprises cooperating key and keyway means on said knob and the boundary edge of said wall opening, the length of the portion of said key and keyway means on said knob being predetermined to prevent disengagement thereof and hence rotation of said knob and said pin whenever said slide is blocked against movement beyond said first displaced position and to permit disengagement of said key and keyway means and hence rotation of said knob and pin only when said slide has been moved past said first and to said second displaced position.

7. A device as claimed in claim 1, wherein said abutment means comprises a rod-shaped member rotatably mounted on said housing and having a manipulating head portion located exteriorly of said housing and an abutment portion located interiorly of said housing and in the path of movement of said slide, said abutment portion having opposed flat faces and a thickness less than but a width substantially equal to the diameter of said rod-shaped member, whereby said abutment portion defines said first displaced position of said slide when said flat faces are oriented in the direction of slide movement and defines said second displaced position of said slide when said flat faces are oriented transversely to the direction of slide movement.

8. A device as claimed in claim 7, wherein said adjustable abutment means further comprises cooperating notch and detent means provided on said rod-shaped member and said housing for preventing, only when interengaged, rotation of said rod-shaped member out of one or the other of its two positions defining the respective orientations of said flat faces of said abutment portion, and spring means acting on said rod-shaped member and biasing the rod shaped member in a direction tending to cause interengagement of said notch and detent means.

9. A device as claimed in claim 8, wherein said manipulating head portion is provided with means for indicating the state of adjustment of said abutment means and hence the orientation of said flat faces of said abutment member to define either said first or said second displaced position of said slide.

10. A device as claimed in claim 1, further comprising a silver alloy tablet supply vial, said adapter having an outer portion connected to said second mounting means and a tubular inner portion projecting through said silver alloy inlet port into said upper housing section, said tubular portion adjacent its lower end having an interior peripheral flange, and said silver alloy tablet supply vial being seated at its bottom end on said flange.

11. A device for dispensing a metered amount of mercury and a metered amount of silver alloy in substantially clump-free powder form, comprising:

a housing having upper and lower interconnected sections;

said upper section being provided with a mercury inlet port, a mercury supply vial, first mounting means associated with said mercury inlet port and supporting said mercury supply vial on said upper housing section in discharging relation to said mercury inlet port, a silver alloy inlet port, a silver alloy powder supply vial, and second mounting means associated with said silver alloy inlet port and supporting said silver alloy powder supply vial on said upper housing section in discharging relation to said silver alloy inlet port;

said lower housing section being provided with a discharge port and with respective means defining first and second passageways ways for enabling gravitational flow of mercury and silver alloy to said discharge port;

means defining a guideway in said housing, a slide mounted in said guideway for reciprocal movement within said housing between a rest position and a displaced position, a knob connected with said slide and projecting exteriorly of said housing for enabling manual displacement of said slide, and spring means arranged in said housing and biasing said slide in the direction of said rest position thereof;

said slide including first and second valve members for controlling the flow of mercury and silver alloy powder, respectively, between said inlet ports and said first and second passageways, said first valve member being provided with a first transverse through opening to constitute a mercury-receiving chamber, and said second valve member being provided with a second through opening to constitute a silver alloy-receiving chamber, said slide when in said rest position thereof disposing said mercury-receiving chamber in communication with said mercury inlet port and said silver alloy-receiving chamber in communication with said second passageway, and said slide when in said displaced position thereof disposing said mercury-receiving chamber in communication with said first passageway and said silver alloy-receiving chamber in communication with said silver alloy inlet port;

said silver alloy powder supply vial having a lower portion extending through said silver alloy inlet port into said upper housing section, a stirring member disposed in said upper housing section and extending up into said silver alloy powder supply vial, and cooperating gear means interconnected between said slide and said stirring member for effecting an oscillatory movement of said stirring member upon reciprocal movement of said slide, thereby to agitate the silver alloy powder and counteract the tendency of the silver alloy powder to clump;

said cooperating gear means comprising a rack and pinion combination, said rack being fixedly secured to and movable with said second valve member, and said pinion being supported by said silver alloy powder supply vial and rotatable relative thereto, said stirring member being fixedly secured to said pinion and movable therewith; and said lower portion of said silver alloy powder supply vial being of reduced diameter relative to the remainder of said silver alloy supply vial and defining an annular shoulder therein, said pinion comprising a tubular hub freely rotatably and axially displaceably extending into said lower portion of said silver alloy powder supply vial, spring means being interposed between said pinion and said silver alloy powder supply vial for biasing said hub of the former outwardly of the latter, and said stirring member being a stiff wire fixedly connected to the interior of said hub and having a pair of mutually inclined portions located within the confines of said silver alloy powder supply vial with the juncture between said mutually inclined portions overlying said shoulder for inhibiting separation of said hub and said pinion from sai silver alloy powder supply vial.

12. In a device for dispensing a metered amount of mercury and a metered amount of silver alloy and including a housing having a mercury inlet port for supporting a mercury supply vial, a silver alloy inlet port for supporting a silver alloy supply vial, a discharge port, respective means defining first and second passageways for enabling gravitational flow of mercury and silver alloy to said discharge port, a slide mounted in said housing for reciprocal movement within said housing between a rest position and a displaced position and including first and second chambered valve members for controlling the flow of mercury and silver alloy, respectively, between said inlet ports and said first and second passageways, said slide when in said rest position thereof disposing the mercury-receiving chamber in communication with said mercury inlet port and the silver alloy-receiving chamber in communication with said second passageway, and said slide when in said displaced position thereof disposing the mercury-receiving chamber in communication with said first passageway and the silver alloy-receiving chamber in communication with said silver alloy inlet port, a knob connected with said slide and projecting exteriorly of said housing for enabling manual displacement of said slide, and means connected with said first valve member and operable by said knob for adjusting the volume of said mercury-receiving chamber; the improvement comprising:

adjustable abutment means mounted in said housing in the path of movement of said slide and operable selectively either to provide a first stop for said slide to define said displaced position thereof or to remove said first stop and provide a second stop for said slide at a point of the movement thereof beyond said displaced position; and means acting on said slide and operable, selectively, for locking said volume adjusting means against shifting whenever said abutment means is adjusted to provide said first stop for said slide and prevent movement of said slide past said displaced position thereof, and for permitting shifting of said volume adjusting means whenever said abutment means is adjusted to provide said second stop for said slide at said point of movement of said slide beyond said displaced position thereof.

13. A device as claimed in claim 12, wherein said adjustable abutment means comprises a rod-shaped member rotatably mounted on said housing and having a manipulating head portion located exteriorly of said housing and an abutment portion located interiorly of said housing and in the path of movement of said slide, said abutment portion having opposed flat faces and a thickness less than but a width substantially equal to the diameter of said rod-shaped member, whereby said abutment portion defines said first stop for said slide when said flat faces are oriented in the direction of slide movement and defines said second stop for said slide when said flat faces are oriented transversely to the direction of slide movement.

14. A device as claimed in claim 13, wherein said adjustable abutment means further comprises cooperating notch and detent means provided on said rod-shaped member and said housing for preventing, only when interengaged, rotation of said rod-shaped member out of one or the other of its two positions defining the respective orientations of said flat faces of said abutment portion, and spring means acting on said rod-shaped member and biasing the same in a direction tending to cause interengagement of said notch and detent means.

15. A device as claimed in claim 14, wherein said manipulating head portion is provided with means for indicating the state of adjustment of said abutment means and hence the orientation of said flat faces of said abutment member to define either said first or said second stop for said slide.

16. A device as claimed in claim 12, wherein said first valve member is a rod connected at one end to said second valve member and having the mercury-receiving chamber located adjacent said one end, said rod further having a longitudinal bore extending from the other end of said rod to the mercury-receiving chamber and being internally threaded adjacent said other end, and said volume adjusting means comprises a pin located in said bore with a close sliding fit and with its tip end region located at the juncture between said bore and the mercury-receiving chamber, said pin further having an intermediate externally threaded region screwed into the threaded section of said bore and having a head end region located exteriorly of said bore beyond said other end of said rod and fixedly connected with said knob, whereby rotation of said knob and therewith or said pin in one sense or the other causes the extent to which said tip end region of said pin projects into the mercury-receiving chamber to be either increased or decreased to either decrease or increase the volume of the mercury-receiving chamber.

17. A device as claimed in claim 16, wherein said knob has a hub extending through a wall opening of said housing, and said locking means comprises cooperating key and keyway means on said knob and the boundary edge of said wall opening, the length of the portion of said key and keyway means on said knob being predetermined to prevent disengagement of said key and keyway means and hence rotation of said knob and said pin whenever said slide is blocked against movement beyond said displaced position thereof by said first stop and to permit disengagement of said key and keyway means and hence rotation of said knob and said pin only when said abutment means is adjusted to remove said first stop and said slide is moved beyond said displaced position to the extent permitted by said second stop.

* * * * *